(12) United States Patent
Kawai

(10) Patent No.: US 7,763,468 B2
(45) Date of Patent: Jul. 27, 2010

(54) SPECIMEN ANALYSIS METHOD AND SPECIMEN ANALYSIS DEVICE

(75) Inventor: Takuji Kawai, Kyoto (JP)

(73) Assignee: ARKRAY, Inc., Kyoto (JP)

(*) Notice: Subject to any disclaimer, the term of this patent is extended or adjusted under 35 U.S.C. 154(b) by 986 days.

(21) Appl. No.: 10/577,578

(22) PCT Filed: Oct. 19, 2004

(86) PCT No.: PCT/JP2004/015415
§ 371 (c)(1), (2), (4) Date: Apr. 27, 2006

(87) PCT Pub. No.: WO2005/040784
PCT Pub. Date: May 6, 2005

(65) Prior Publication Data
US 2007/0031971 A1 Feb. 8, 2007

(30) Foreign Application Priority Data
Oct. 29, 2003 (JP) .............................. 2003-368888

(51) Int. Cl.
G01N 27/27 (2006.01)
G01N 27/06 (2006.01)
G01N 33/50 (2006.01)

(52) U.S. Cl. .................... 436/55; 422/68.1; 422/82.01; 422/82.02; 436/34; 436/46; 436/50; 436/95; 436/149; 436/150; 436/151

(58) Field of Classification Search ............. 422/56–58, 422/68.1, 82.01–82.03; 436/34, 46, 50, 55, 436/95, 149–151, 183
See application file for complete search history.

(56) References Cited

U.S. PATENT DOCUMENTS

| 5,243,516 | A | | 9/1993 | White |
| 5,320,732 | A | | 6/1994 | Nankai et al. |
| 5,344,754 | A | * | 9/1994 | Zweig ........................... 435/4 |
| 5,352,351 | A | | 10/1994 | White et al. |
| 6,069,011 | A | * | 5/2000 | Riedel ......................... 436/34 |
| 6,193,873 | B1 | * | 2/2001 | Ohara et al. ................ 205/792 |
| 6,645,368 | B1 | * | 11/2003 | Beaty et al. ................ 205/792 |
| 6,743,635 | B2 | * | 6/2004 | Neel et al. .................... 436/95 |
| 6,872,299 | B2 | * | 3/2005 | Kermani et al. ......... 205/777.5 |
| 6,875,327 | B1 | * | 4/2005 | Miyazaki et al. ....... 204/403.14 |
| 7,338,639 | B2 | * | 3/2008 | Burke et al. ............. 422/82.01 |
| 2002/0092612 | A1 | * | 7/2002 | Davies et al. ............... 156/292 |
| 2002/0133064 | A1 | | 9/2002 | Ueno et al. |

FOREIGN PATENT DOCUMENTS

| JP | 3-287064 | 12/1991 |
| JP | 5-502727 | 5/1993 |
| JP | 8-10208 | 1/1996 |
| JP | 8-205589 | 3/1996 |
| JP | 11-174022 | 7/1999 |
| JP | 2002-340853 | 11/2002 |

* cited by examiner

Primary Examiner—Arlen Soderquist
(74) Attorney, Agent, or Firm—Hamre, Schumann, Mueller & Larson, P.C.

(57) ABSTRACT

The present invention relates to a technique for analyzing a sample by utilizing a double integration circuit (11) for outputting a physical quantity related to the output from an analytical tool (2). In the present invention, the time interval from when the output from the analytical tool (2) is inputted into the double integration circuit (11) till when the physical quantity is started to be outputted from the double integration circuit (11) differs before and after the supply of the sample to the analytical tool (2) is confirmed.

11 Claims, 11 Drawing Sheets

SPECIMEN ANALYSIS METHOD AND SPECIMEN ANALYSIS DEVICE

TECHNICAL FIELD

The present invention relates to a technique for analyzing a particular component (e.g. glucose, cholesterol or lactic acid) in a sample (biochemical sample such as blood or urine)

BACKGROUND ART

Figure 11A:
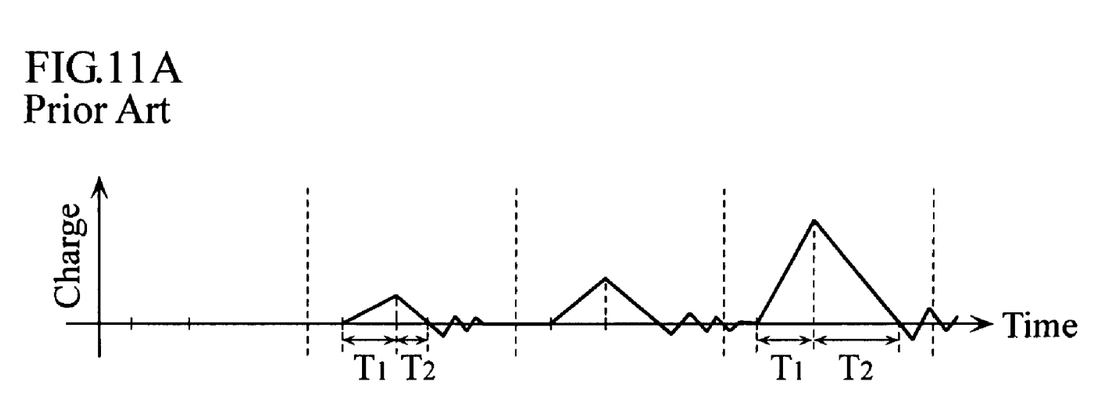
Figure 11B:
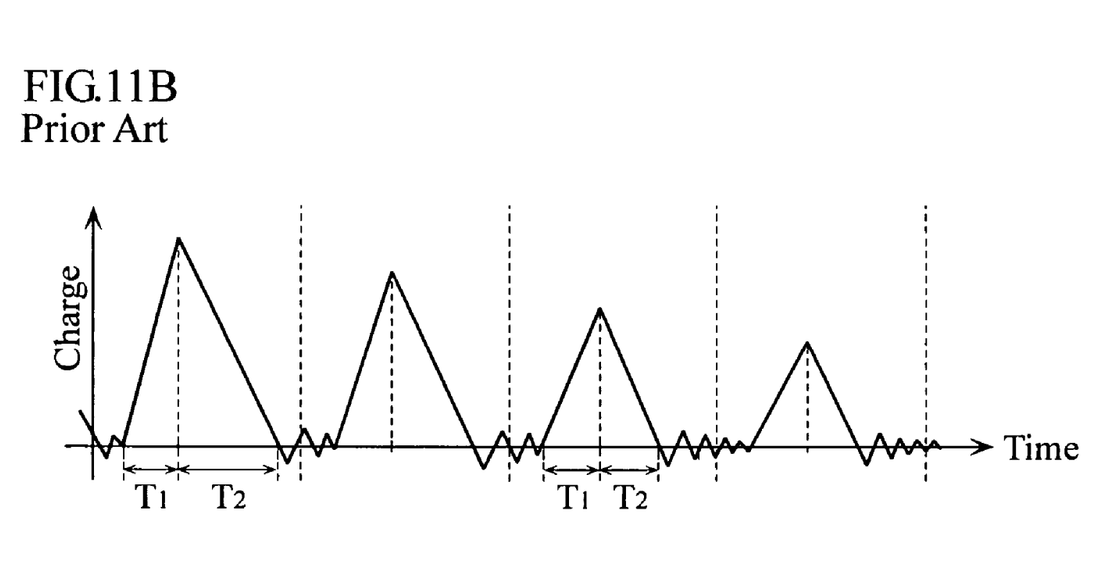
FIG. 11B shows the output waveform after the blood supply is confirmed.
Figure 12:
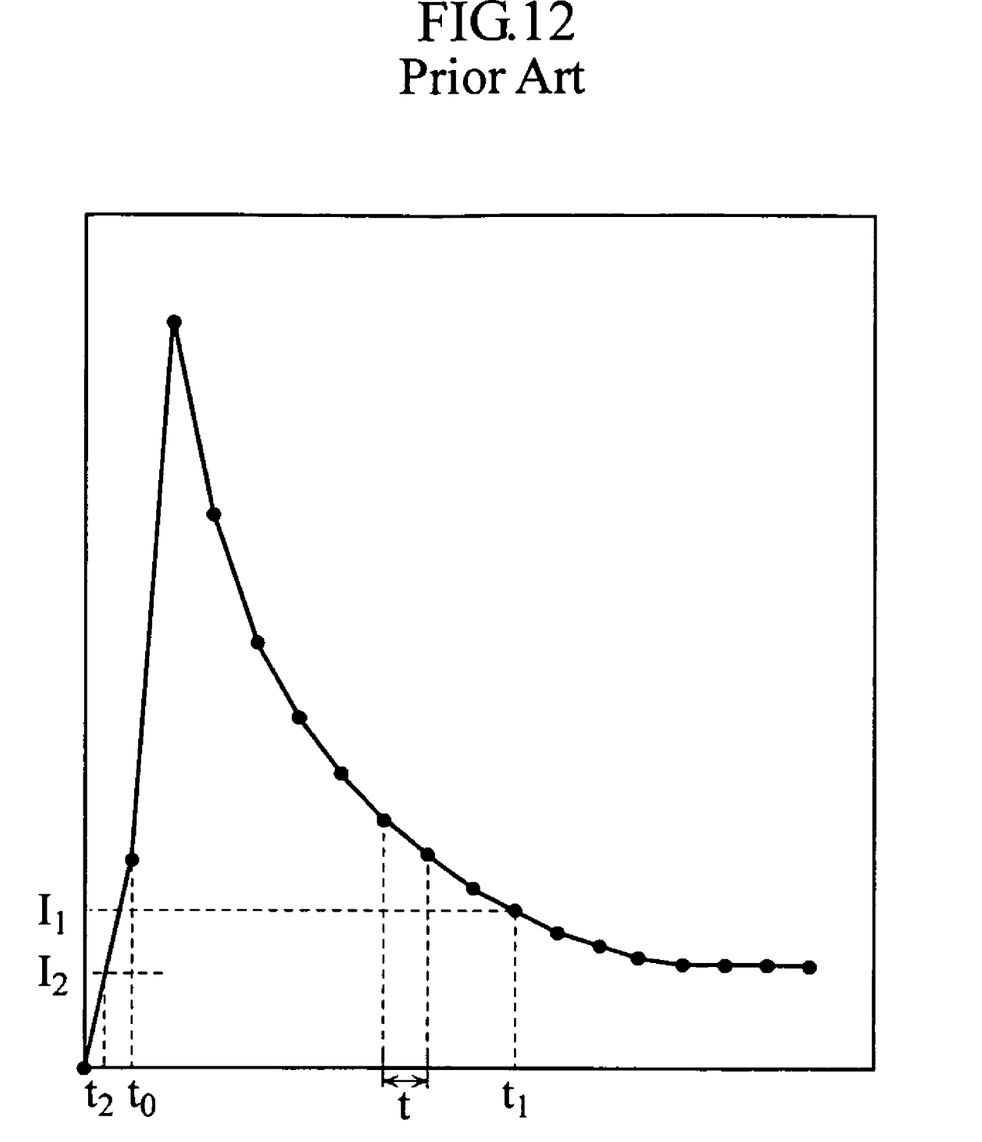
FIG. 12 is a graph showing the change with time of a response value in the prior-art analytical apparatus.

As an easy method to measure the glucose level in blood, a disposable glucose sensor is often utilized (See Patent Document 1, for example). For instance, the glucose sensor may be designed to output the response current, which is necessary for computing the blood glucose level, when it is mounted to an analytical apparatus. In the analytical apparatus, the magnitude of the response current is determined by utilizing a double integration circuit including a capacitor, and the blood glucose level is computed based on the determined response current. As shown in FIGS. 11A and 11B, the magnitude of the response current is determined based on the discharge time ($T_2$) of the capacitor after the capacitor is charged with the electric charge related with the response current for a predetermined time period ($T_1$). As shown in FIG. 12, the determination of the response current is performed at predetermined time intervals (t). On the other hand, the response current ($I_1$) for computing the blood glucose level is sampled at the time ($t_1$) after a predetermined time period has elapsed from the time ($t_0$) when the supply of the blood to the glucose sensor was confirmed. The blood supply to the glucose sensor is confirmed by checking whether or not the response current measured exceeds a predetermined threshold ($I_2$).

To accurately determine the response value by the method utilizing the double integration circuit, it is preferable to set the charge time ($T_1$) of the capacitor relatively long. Therefore, for the measurement accuracy of the response current, the time interval (t) for measuring the response current need be set relatively long.

As will be understood from FIG. 12, in the initial stage in which the blood is supplied to the glucose sensor, the response current increases sharply. Therefore, in the case where the time interval (t) for measuring the response current is set long, the time when the blood is supplied cannot be determined accurately. Due to such inaccuracy, the time period from when the sample is supplied till when the response current for the computation is sampled may vary among the measurements, which may degrade the measurement accuracy of the blood glucose level.

Patent Document 1: JP-B-H08-10208

DISCLOSURE OF THE INVENTION

An object of the present invention is to enhance the accuracy of sample analysis by accurately finding the time when the sample is supplied to the analytical tool and the output from the analytical tool to be used for the computation.

According to a first aspect of the present invention, there is provided a sample analysis method comprising a first step of confirming that a sample is supplied to an analytical tool based on output from the analytical tool, a second step of grasping a level of the output from the analytical tool in a predetermined time period after the supply of the sample to the analytical tool is confirmed, the grasping being performed at least once including at a time point when the predetermined time period has elapsed, and a third step of performing computation necessary for the analysis of the sample. The grasping of the output from the analytical tool in the first step and the second step is performed based on output from a double integration circuit which is obtained by inputting the output from the analytical tool into the double integration circuit. The first step comprises grasping a level of the output from the double integration circuit repetitively at first time intervals each defined by a time period from when the inputting into the double integration circuit is started till when the outputting from the double integration circuit is finished. In grasping the level of the output from the double integration circuit in the second step, a second time interval defined by a time period from when the inputting into the double integration circuit is started till when the outputting from the double integration circuit is finished is set longer than the first time interval.

For instance, in the second step, the output from the analytical tool at the time point when the predetermined time period has elapsed is grasped by performing the inputting of the output from the analytical tool into the double integration circuit and the outputting from the double integration circuit repetitively at the second time intervals.

Preferably, the first time interval is selected from the range of 10 to 30 msec, whereas the second time interval is selected from the range of 30 to 300 msec.

For instance, the double integration circuit to be used includes a capacitor for storing the output from the analytical tool as electric charge and then discharging the stored electric charge and is capable of grasping the output from the analytical tool based on the discharge time of the capacitor. In this case, the charge time of the capacitor in the first time interval in the first step is shorter than charge time of the capacitor in the second time interval in the second step. Preferably, the charge time of the capacitor in the first time interval in the first step is selected from the range of 5 to 15 msec, whereas the charge time of the capacitor in the second time interval in the second step is selected from the range of 15 to 150 msec.

For instance, the analytical tool to be used includes an electrode for outputting electric physical quantity. Preferably, the analytical tool to be used includes a reagent portion-containing at least one reagent for promoting the electron transfer between the particular component and the electrode, and an additional electrode for applying, together with the electrode, voltage to a coexistence system of the sample and the at least one reagent. In this case, in the analytical tool, the electric physical quantity is outputted from the electrode as a current by applying voltage to the coexistence system using the electrode and the additional electrode.

Preferably, the analytical tool to be used is designed to use e.g. blood as the sample. The present invention is also applicable to the use of an analytical tool designed to use a sample other than blood, i.e., urine or saliva, for example.

According to a second aspect of the present invention, there is provided a sample analysis apparatus to be used with an analytical tool mounted thereto for analyzing a sample supplied to the analytical tool based on output from the analytical tool. The apparatus comprises a double integration circuit into which the output from the analytical tool is inputted and which outputs a physical quantity related to the input, and a controller for controlling the timing at which the output from the analytical tool is inputted into the double integration circuit and the timing at which the physical quantity is outputted from the double integration circuit. The controller performs control so that a time interval from the start of the inputting into the double integration circuit till the start of the outputting from the double integration circuit becomes longer in the state after the supply of the sample to the analytical tool is confirmed than in the state before the supply of the sample to the analytical tool is confirmed.

For instance, the double integration circuit includes a capacitor for storing the output from the analytical tool as electric charge and then discharging the stored electric charge and is capable of grasping the output from the analytical tool based on the discharge time of the capacitor. In this case, the controller performs control so that the charge time of the capacitor becomes longer in the state after the supply of the sample to the analytical tool is confirmed than in the state before the supply of the sample to the analytical tool is confirmed.

When the analytical tool includes an electrode for outputting an electric physical quantity, the sample analysis apparatus of the present invention further comprises a switch for selecting the state in which the double integration circuit is directly or indirectly connected to ground or the state in which the double integration circuit is connected to the electrode. In this case, the controller controls the switch to control the timing at which the output from the analytical tool is inputted into the double integration circuit and the timing at which the physical quantity is outputted from the double integration circuit.

Herein, the state in which the double integration circuit is indirectly connected to ground means the state in which a reference supply intervenes between the double integration circuit and the ground.

BRIEF DESCRIPTION OF THE DRAWINGS

FIGS. 6 show output waveforms of the A/D converter, and FIG. 6A shows the output waveform before the blood supply to the biosensor is confirmed, whereas

FIG. 7A shows the output waveform of one cycle before the confirmation of the blood supply, whereas

FIGS. 11 show output waveforms of a double integration circuit in a prior-art analytical apparatus, and FIG. 11A shows the output waveform before the blood supply is confirmed, whereas

BEST MODE FOR CARRYING OUT THE INVENTION

Figure 1:
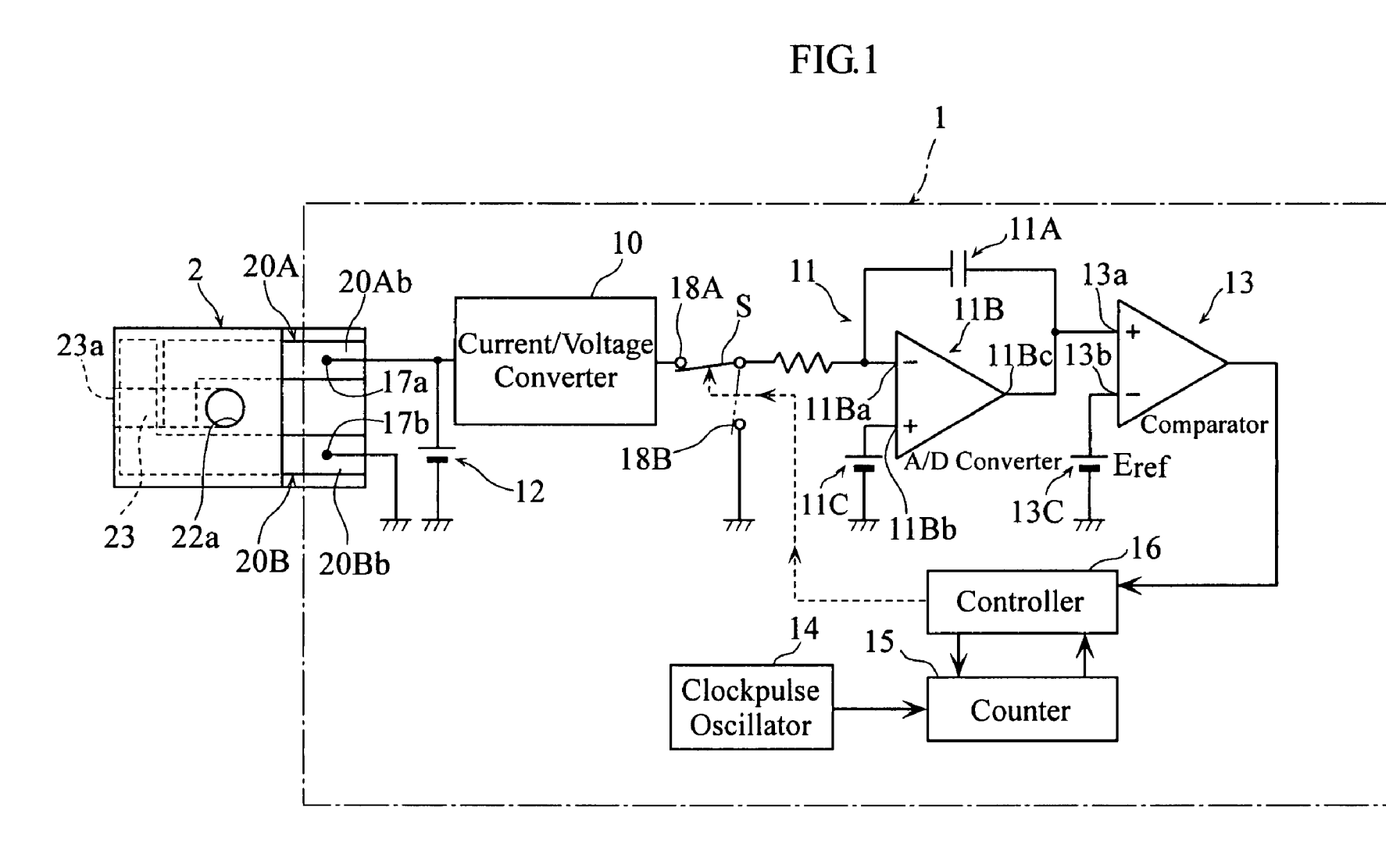
FIG. 1 is a conceptual view showing an analytical apparatus according to the present invention in a state in which a biosensor is mounted.

As shown in FIG. 1, the analytical apparatus 1, which is used with a biosensor 2 mounted thereto, includes a current/voltage converting circuit 10, an A/D converter 11, a circuit power source 12, a comparator 13, a clockpulse oscillator 14, a counter 15 and a control circuit 16.

Figure 2:
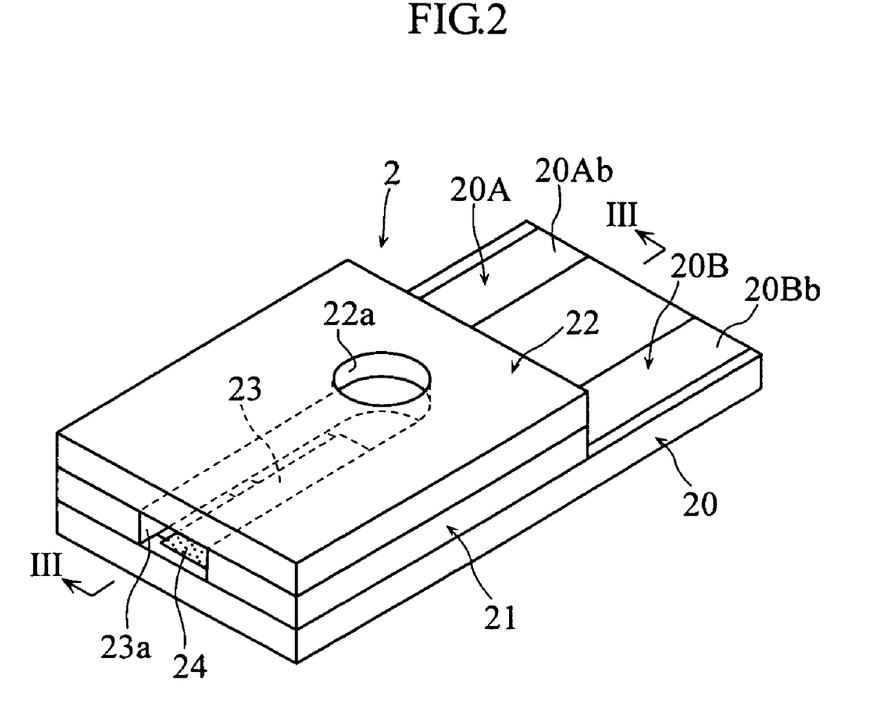
FIG. 2 is an overall perspective view of the biosensor shown in FIG. 1.
Figure 3:
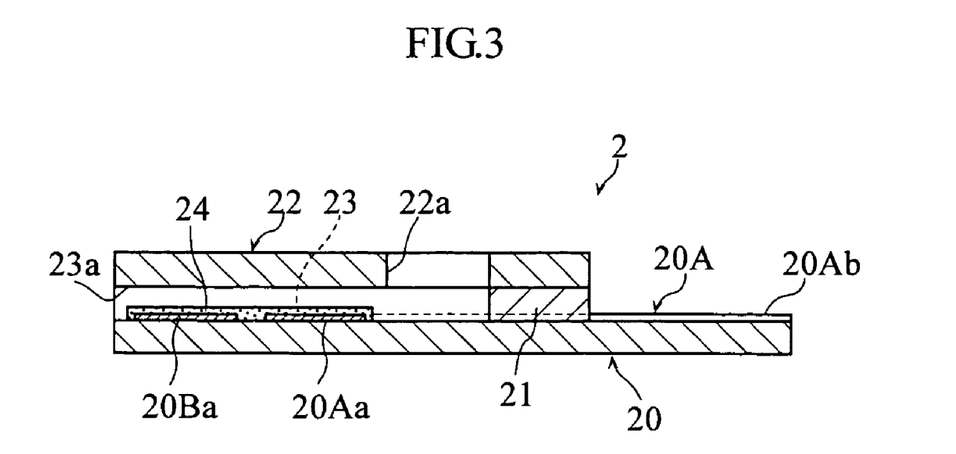
FIG. 3 is a sectional view taken along lines III-III in FIG. 2.
Figure 4:
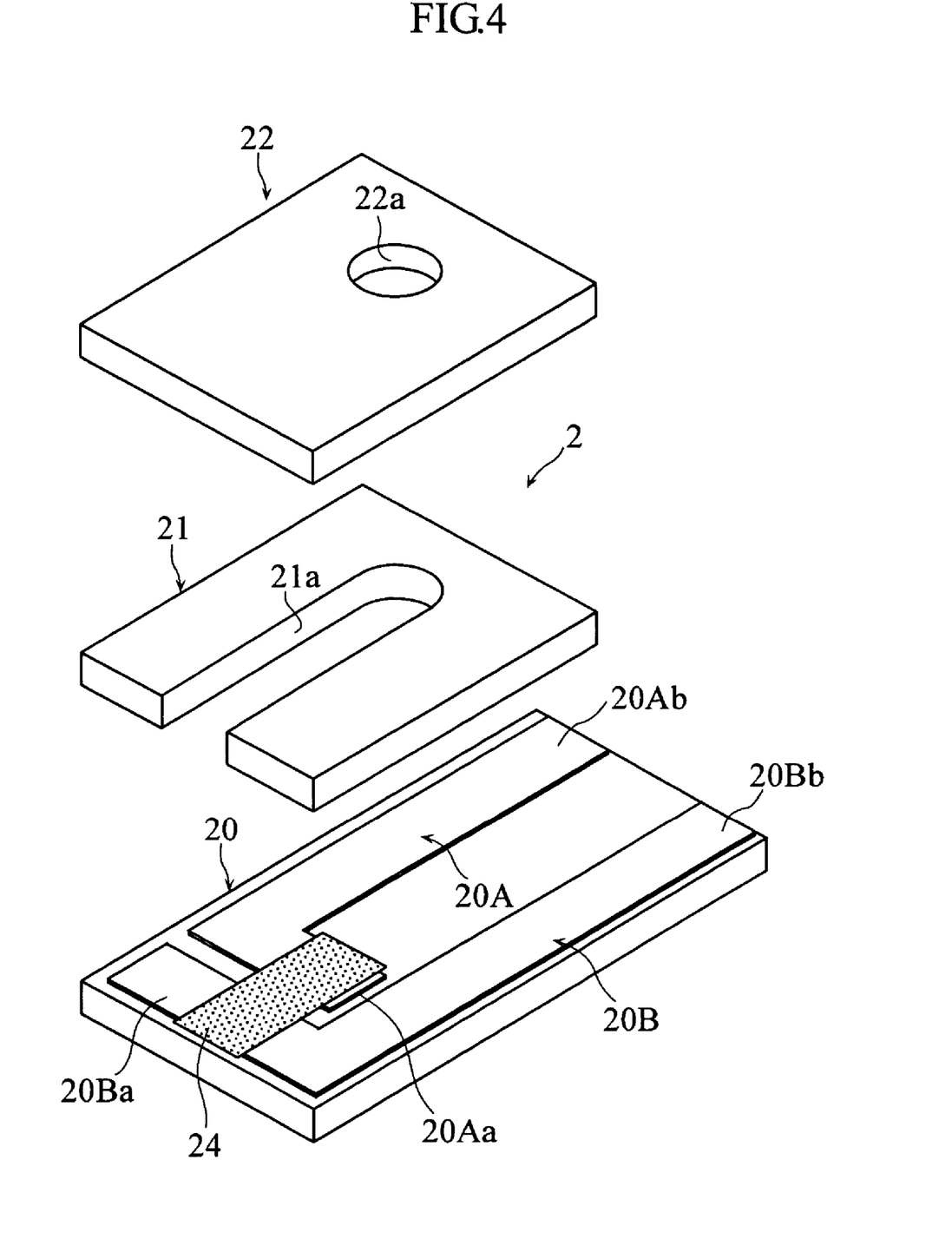
FIG. 4 is an exploded perspective view of the biosensor shown in FIG. 2.

The biosensor 2 used in the analytical apparatus 1 functions to analyze a particular component contained in a sample (e.g. blood) by an electrochemical method and is designed to be disposable. As shown in FIGS. 2 through 4, the biosensor 2 comprises a substrate 20 and a cover 22 stacked thereon via a spacer 21 formed with a slit 21a. The above-described elements 20-22 define a flow path 23. The flow path 23 is provided for moving the sample introduced through a sample introduction port 23a toward a hole 22a of the cover 22 by utilizing capillary action and for providing a reaction field for the sample and a reagent.

The substrate 20 is formed with a working electrode 20A and a counter electrode 20B for applying a voltage to the reaction filed. The working electrode 20A and the counter electrode 20B have respective first ends 20Aa and 20Ba which are connected to each other by a reagent portion 24. As better shown in FIG. 1, the working electrode 20A and the counter electrode 20B have respective second ends 20Ab and 20Bb which are brought into contact with a first and a second terminals 17a and 17b of the analytical apparatus 1 when the biosensor 2 is mounted to the analytical apparatus 1. For instance, the reagent portion 24 is in a solid state including an oxidoreductase and an electron mediator and is soluble when the sample is supplied thereto. The kinds of oxidoreductase and electron mediator are selected depending on e.g. the kind of the component (particular component) to be measured. For example, to measure the glucose level, glucose dehydrogenase or glucose oxidase is used as the oxidoreductase, whereas potassium ferricyanide is used as the electron mediator.

The current/voltage converting circuit 10 shown in FIG. 1 functions to convert information obtained from the biosensor 2 as a current value into a voltage value for inputting into the A/D converter 11.

The A/D converter 11 functions to convert the inputted analog value to a digital value for outputting and is structured as a double integration circuit. The A/D converter 11 comprises a capacitor 11A and an operational amplifier 11B which includes an inverting input 1Ba and a non-inverting input 11Bb. The operational amplifier 11B is connectable to terminals 18A, 18b via a switch S. Therefore, in the operational amplifier 11B, by selectively connecting the switch S to the terminal 18A or the terminal 18B, the inverting input 11Ba is selectively connected to the current/voltage converting circuit 10 or ground. The non-inverting input 11Bb is connected to a first reference supply 11C. Therefore, the capacitor 11A is charged when connected to the current/voltage converting circuit 10 and discharged when connected to the first reference supply 11C. The output 11Bc of the A/D converter 11 is connected to a non-inverting input 13a of the comparator 13, which will be described later. To the non-inverting input 13a, the discharge from the capacitor 11A (the potential difference at the capacitor 11A), i.e., the output related with the output from the biosensor 2 is inputted.

The circuit power source 12 functions to apply a voltage to the biosensor 2 and supply power to electronic components. As the circuit power source 12, use may be made of a DC power source such as a dry cell.

The comparator 13 is provided to grasp the output from the A/D converter 11 (operational amplifier 11B), i.e., the output of the biosensor 2. The non-inverting input 13a of the comparator 13 is connected to the A/D converter 11 (operational amplifier 11B), whereas the inverting input 13b is connected to a second reference supply 13C. Thus, the comparator 13 determines whether or not the output from the A/D converter 11 (operational amplifier 11B) is greater than the power supply voltage of the second reference supply 13C. When the output from the A/D converter 11 (operational amplifier 11B) is greater than the power supply voltage of the second reference supply 13C, the comparator 13 outputs the signal "1". When the above-described output is not greater than the power supply voltage of the second reference supply 13C, the comparator outputs the signal "0".

The clockpulse oscillator 14 generates a clockpulse signal to be supplied to the counter 15 at a predetermined period.

Under the control of the control circuit 16, the counter 15 counts the number of clockpulse signals from particular reference time.

The control circuit 16, which serves to control various elements, comprises a CPU, a ROM and a RAM, for example. For instance, the control circuit 16 checks and resets the number of clockpulse signals at the counter 15, changes the state of the switch S or computes the concentration of a particular component contained in a sample.

Figure 5:
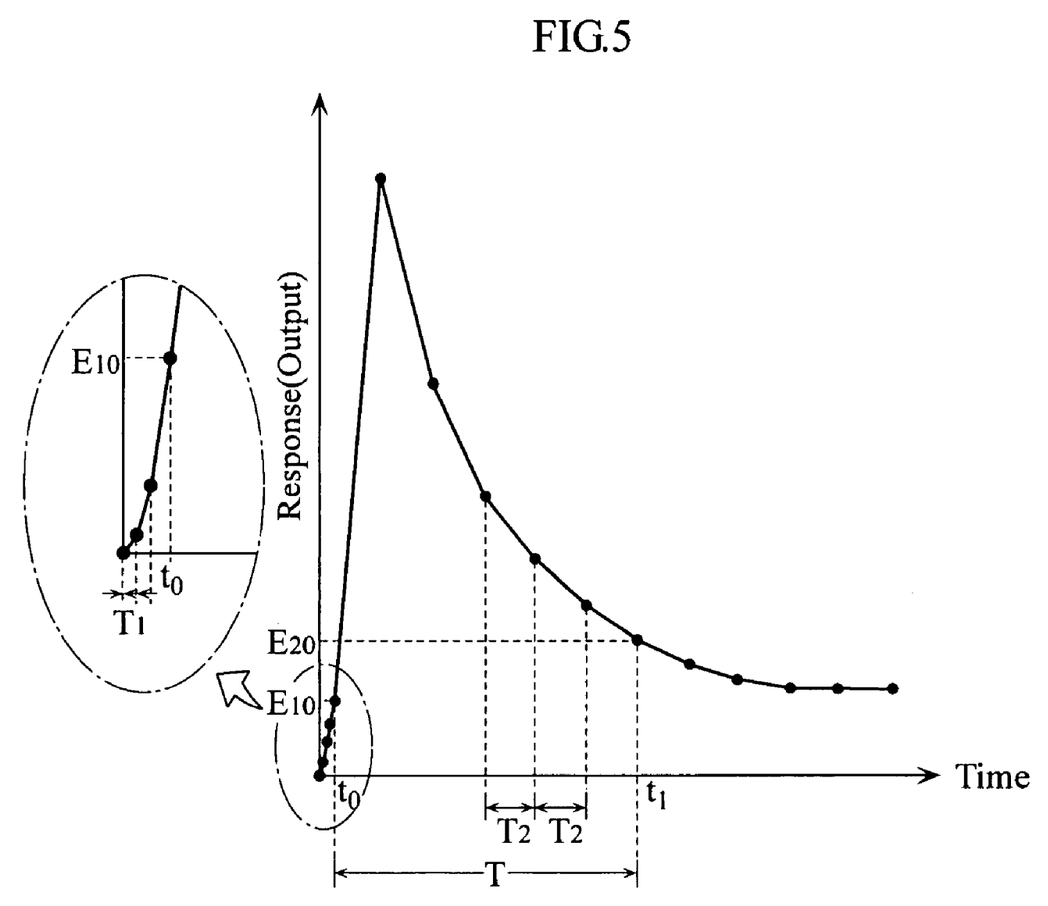
FIG. 5 is a graph showing the change with time of a response value.

FIG. 5 shows an example of change with time of the output (response current) from the biosensor 2. The concentration of a particular component is computed at the control circuit 16 based on the response current outputted from the biosensor 2 at the time ($t_1$) after a predetermined time period T has elapsed from the time ($t_0$) at which the supply of the sample to the biosensor 2 was confirmed. The control circuit 16 grasps the response current as a voltage value. The timing at which the voltage value is to be measured, for example, is controlled by the control circuit 16.

Figure 6A:
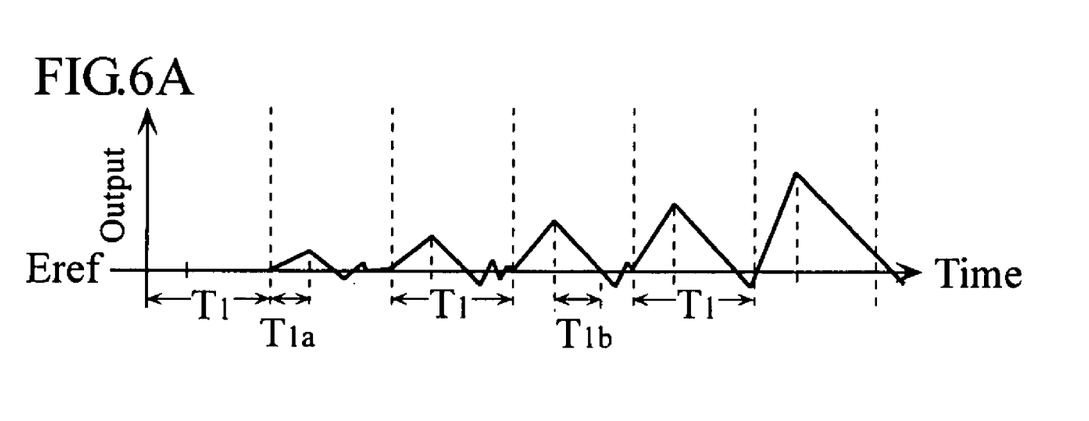

As shown in FIGS. 5 and 6A, the supply of the sample is confirmed by sampling the response current at predetermined intervals of time ($T_1$) and determining whether or not the response current exceeds a threshold. Each interval of time ($T_1$) for sampling the response current may be set to 10 to 30 msec, for example.

Figure 7A:
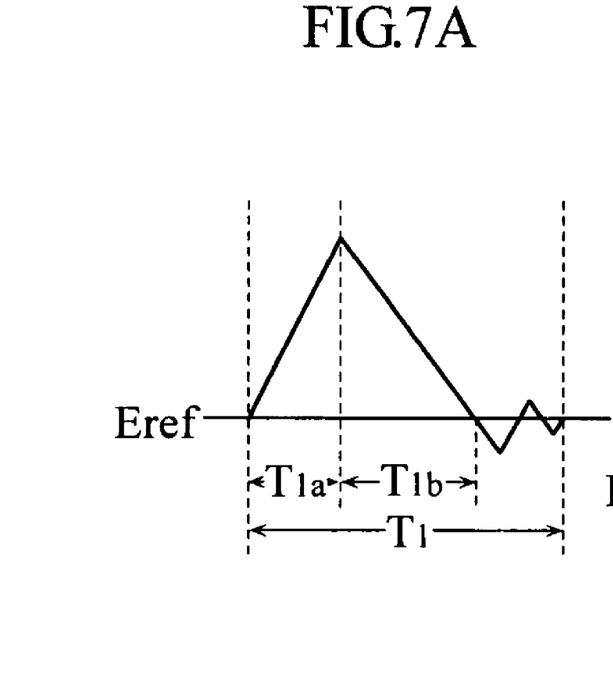

To grasp the response current for confirming the sample supply, the switch S is first connected to the terminal 18A, as indicated by a solid line in FIG. 1, to connect the A/D converter 11 to the biosensor 2. Thus, as shown in FIG. 7A, the output (electric charge) from the biosensor 2 is stored in the capacitor 11A for a predetermined time period (charge time) ($T_{1a}$). The charge time ($T_{1a}$) may be set to 5 to 15 msec, for example. Subsequently, as indicated by a phantom line in FIG. 1, the switch S is connected to the terminal 18B to connect the A/D converter 11 to ground, thereby causing the capacitor 11A to discharge. The control circuit 16 computes, based on the output from the comparator 13, the discharge time ($T_{1b}$) taken for the output from the A/D converter 11 to drop to the power supply voltage of the second reference supply 13C (See FIG. 7A). Provided that the charge time ($T_{1a}$) and the power supply voltage ($E_{ref}$) of the second reference supply 13C are constant, the discharge time ($T_{1b}$) is proportional to the electric charge stored in the capacitor 11A, i.e., the output from the biosensor 2 in the charge time ($T_{1a}$). Therefore, in the control circuit 16 shown in FIG. 1, the response current (output from the biosensor 2) is grasped as a voltage ($E_1$) related with the discharge time ($T_{1b}$).

As will be understood from FIGS. 5 and 7A, in the control circuit 16, every time the responsive current for computation is grasped as a voltage value ($E_1$), the voltage value ($E_1$) is compared with a threshold ($E_{10}$). When the grasped voltage value ($E_1$) exceeds the threshold ($E_{10}$), it is determined that the sample is supplied to the biosensor 2. However, in the case where the output from the A/D converter 11 does not drop to the power supply voltage of the second reference supply 13C even after a predetermined time period has elapsed, it can be judged that the charge of the capacitor 11A is large and the output from the biosensor 2 is high. In such a case, the control circuit 16 may judge, without conducting the comparison with the threshold ($E_{10}$), that the sample is supplied to the biosensor 2.

Figure 6B:
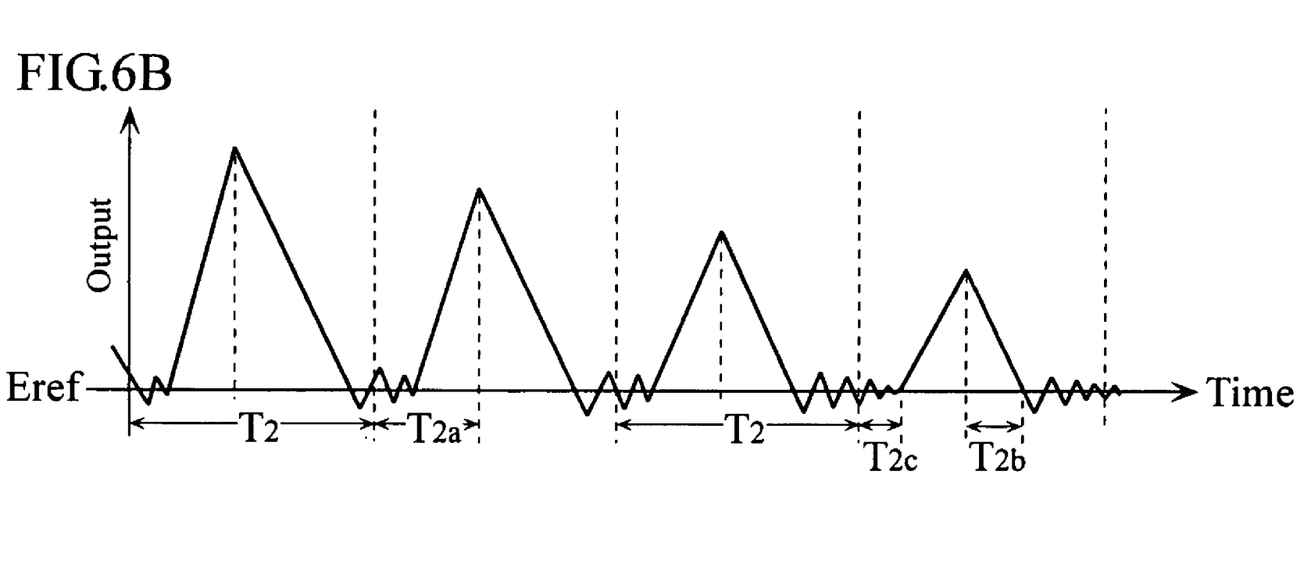
FIG. 6B shows the output waveform after the blood supply to the biosensor is confirmed.

As shown in FIGS. 5 and 6B, the response current for the computation of the concentration is measured at predetermined intervals of time ($T_2$) after the time ($t_0$) at which the supply of the sample to the biosensor 2 was confirmed, and the response current at the time ($t_1$) when a predetermined time period ($T(=t_1-t_0)$) has elapsed from the confirmation of the sample supply is grasped. As will be understood from the comparison of FIG. 7A and FIG. 7B, the response current in this case is grasped similarly to the response current for confirming the sample supply. However, the technique for grasping the response current for the concentration computation differs from the technique for obtaining the response current for the confirmation of sample supply in the following points. Firstly, the time interval ($T_2$) for sampling the response current for the computation is set to 30 to 300 msec, for example, which is longer than the time interval ($T_1$) for grasping the response current for the confirmation of sample supply. Secondly, the charge time ($T_{2a}$) for storing the output (electric charge) from the biosensor 2 in the capacitor 11A is set to 15 to 150 msec, which is also longer than the charge time ($T_{1a}$) for grasping the response current for the sample supply confirmation. Thirdly, settling time ($T_{2c}$) is provided as the preceding stage of charging the capacitor 11A to sufficiently stabilize the charge amount of the capacitor 11A before charging the capacitor 11A.

With respect to the response current for the computation of the concentration as well, provided that the charge time ($T_{2a}$) and the power supply voltage ($E_{ref}$) of the second reference supply 13C are constant, the discharge time ($T_{2b}$) is proportional to the electric charge stored in the capacitor 11A, i.e., the output from the biosensor 2 in the charge time ($T_{2a}$). Therefore, in the control circuit 16 shown in FIG. 1, the response current (output from the biosensor 2) is grasped from the discharge time ($T_{1b}$) as a voltage ($E_2$).

The concentration of a particular component in the sample is computed in the control circuit 16 by applying the voltage value ($E_2$) to an analytical curve prepared in advance. For instance, the calibration curve is prepared as a function or a measurement table showing the relationship between voltage value (E2) and concentration of the particular component and stored in a memory in the control circuit 16.

A method for measuring a blood glucose level using the biosensor 2 and the analytical apparatus 1 will be described below. In the following description of the blood glucose level measurement method, FIG. 1 and the designated figures should be referred to. Further, it is assumed that, in the analytical apparatus 1 before the biosensor 2 is mounted, the switch S is connected to the terminal 18A so that the current/voltage converting circuit 10 is connected to the A/D converter 11.

To measure the blood glucose level using the analytical apparatus 1, the user mounts the biosensor 2 to the analytical apparatus 1 and introduces blood into the flow path 23 through the sample introduction port 23a of the biosensor 2 (See FIG. 3). In the flow path 23, the blood travels toward the hole 22a by capillary action.

Figure 8:
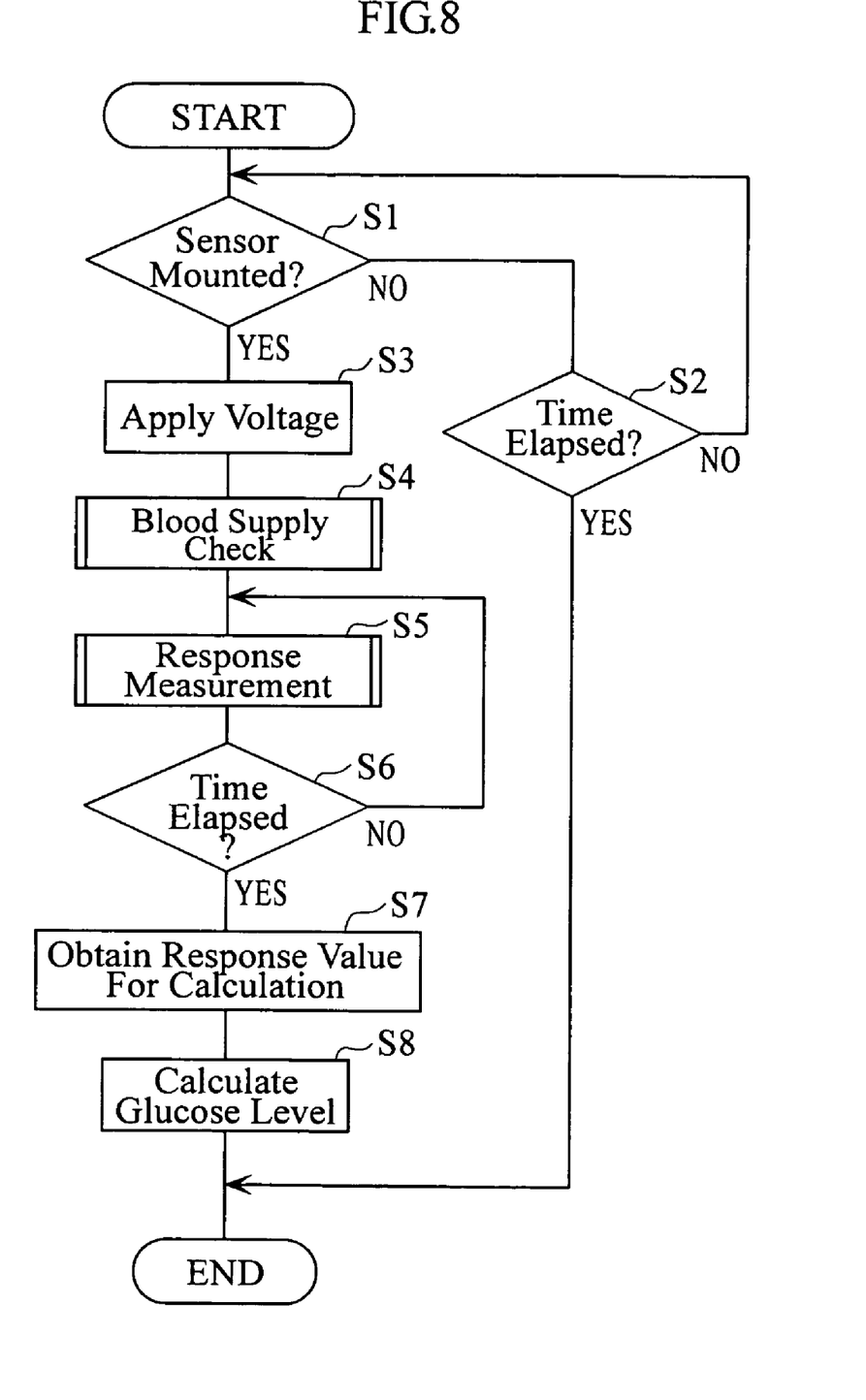
FIG. 8 is a flowchart showing the process of blood glucose level measurement in the analytical apparatus.

As shown in FIG. 8, in the analytical apparatus 1, whether or not the biosensor 2 is mounted is determined in the control circuit 16 (S1). Specifically, a detection sensor such as a pressure sensitive sensor or a photo sensor may be provided at a portion in the analytical apparatus 1 at which the biosensor 2 is to be mounted, and the above-described determination may be made based on the output from the detection sensor.

Alternatively, the user may operate a button to make the control circuit to recognize that the biosensor 2 is mounted to the analytical apparatus 1.

In the analytical apparatus 1, when it is determined that the biosensor 2 is not mounted (S1: NO), a determination is made as to whether or not a predetermined time period has-elapsed from when the power was turned on (S2). When it is determined in the analytical apparatus 1 that the predetermined time period has not elapsed from when power was turned on (S2: NO), whether or not the biosensor 2 is mounted is determined (S1). When it is determined in the analytical apparatus 1 that the predetermined time period has elapsed from when the power was turned on (S2: YES), the analysis operation is not performed.

When it is determined in the analytical apparatus 1 that the biosensor 2 is mounted (S1: YES), a voltage is applied across the working electrode 20A and the counter electrode 20B of the biosensor 2 (S3) Then, whether or not blood is supplied to the biosensor 2 is checked (S4). The voltage application across the working electrode 20A and the counter electrode 20B may be started before the mounting of the biosensor 2 is confirmed in the analytical apparatus 1, i.e., from the time when the biosensor 2 is mounted to-the analytical apparatus 1.

To confirm the supply of the sample in S4, the current generated due to the liquid conduction between the working electrode 20A and the counter electrode 20B (see FIGS. 3 and 4) by the blood is grasped as a voltage value at a plurality of measurement points with predetermined time intervals ($T_1$) as shown in FIG. 5, and whether or not the voltage value exceeds a predetermined value (threshold) ($E_{10}$) is checked. Thus, in the control circuit 16, whether or not the blood has reached the working electrode 20A is determined by checking the liquid conduction between the working electrode 20A and the counter electrode 20B.

Figure 9:
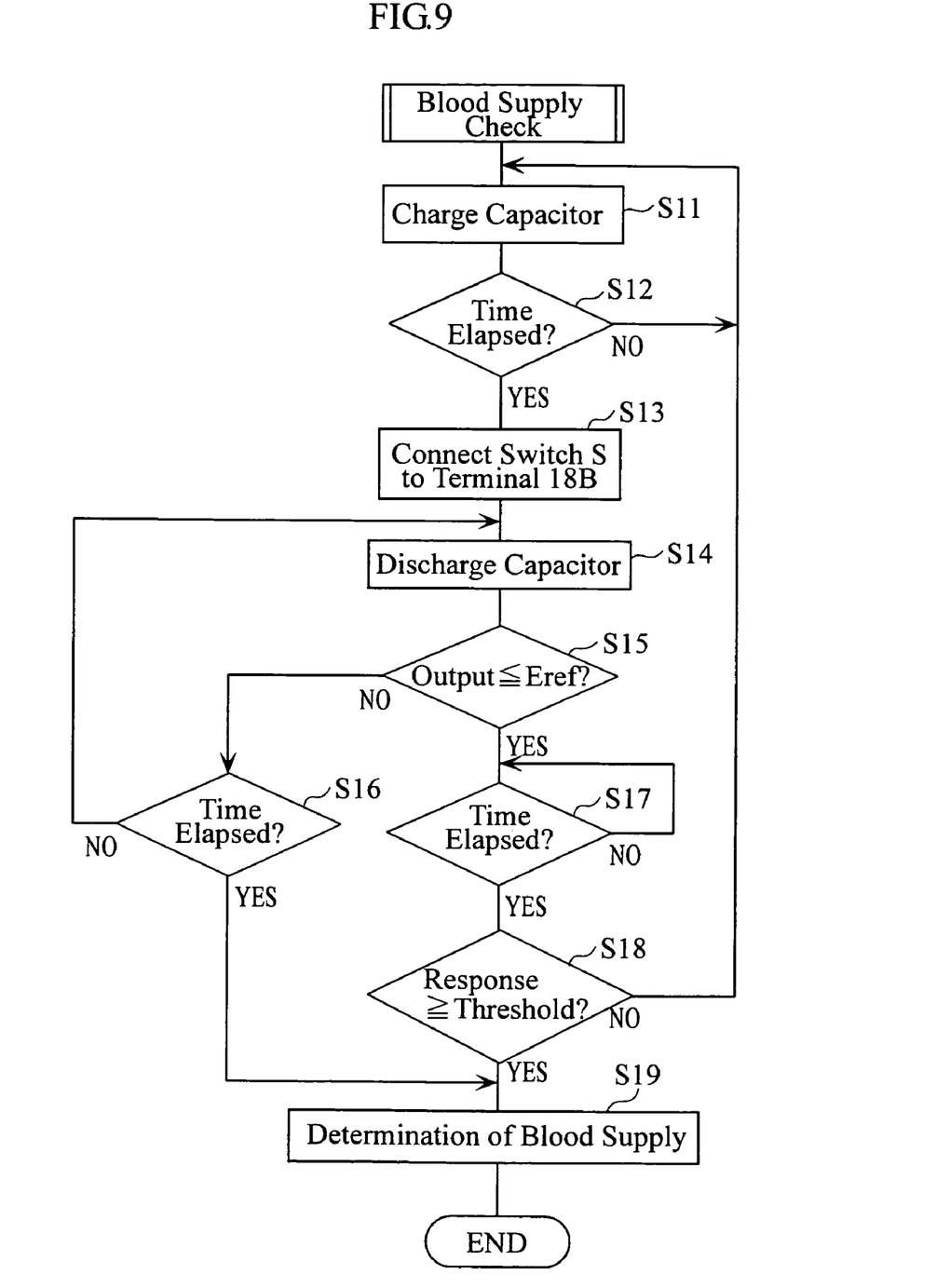
FIG. 9 is a flowchart showing the process of blood supply confirmation in the analytical apparatus.

To grasp the voltage value, as shown in FIGS. 6A and 9, electric charge due to the current generated in the biosensor 2 is stored in the capacitor 11A of the A/D converter 11 for a predetermined time period ($T_{1a}$) from a target measurement point (S11, S12). Whether or not the predetermined time period ($T_{1a}$) has elapsed is determined by counting, at the counter 15, the number of clockpulses generated from the clockpulse oscillator 14 and checking whether or not the count number at the counter 15 has reached the count number corresponding to the time period ($T_{1a}$). This check is repetitively performed (S12) until it is determined in the control circuit 16 that the predetermined time period ($T_{1a}$) has elapsed (S12: YES).

When it is determined in the control circuit 16 that the predetermined time period ($T_{1a}$) has elapsed (S12: YES), the switch S is connected to the terminal 18B under the control of the control circuit 16 (S13). As a result, the inverting input 11Ba of the A/D converter is grounded, whereby the electric charge is discharged from the capacitor 11A (S14).

In the control circuit 16, whether the output from the comparator 13 is "1" or "0" is checked. Specifically, in the control circuit 16, when the output from the comparator 13 is recognized as "1", the output from the A/D converter 11 is determined to be greater than the reference supply value ($E_{ref}$) of the second reference supply 13C (S15: NO) When the output from the comparator 13 is recognized as "0", the output from the A/D converter 11 is determined to be not greater than the reference supply value ($E_{ref}$) of the second reference supply 13C (S15: YES).

When it is determined in the control circuit 16 that the output from the A/D converter 11 is greater than the reference supply value ($E_{ref}$) of the second reference supply 13C (S15: NO), whether or not a predetermined time period (=$T_1$-$T_{1a}$) (See FIG. 7A) has elapsed from the start of the discharge is determined (S16). When it is determined in the control circuit 16 that the predetermined time period (=$T_1$-$T_{1a}$) (See FIG. 7A) has not elapsed from the start of the discharge (S16: NO), the process step of S15 or S16 is repeated until it is determined that the output from the A/D converter 11 is not greater than the reference supply value ($E_{ref}$) of the second reference supply 13C (S15: YES) or that the predetermined time period (=$T_1$-$T_{1a}$) (See FIG. 7A) has elapsed from the start of the discharge (S16: YES).

When it is determined in the control circuit 16 that the output from the A/D converter 11 is not greater than the reference supply value ($E_{ref}$) of the second reference supply 13C (S15: YES), a determination is made as to whether or not the predetermined time period (=$T_1$-$T_{1a}$) has elapsed from the start of the discharge, i.e., whether or not the sampling time ($T_1$) is finished (S17). The determination of S17 is repeated until it is determined in the control circuit 16 that the sampling time ($T_1$) is finished (S17: YES).

When it is determined in the control circuit 16 that the sampling time ($T_1$) is finished (S17: YES), a determination is made as to whether or not the response value from the biosensor 2 exceeds the threshold ($E_{10}$) (See FIG. 5) (S18). The determination is made by grasping the response current from the biosensor 2 as a voltage value and checking whether or not the voltage value exceeds the threshold ($E_{10}$) (See FIG. 5). To obtain the response current, in the control circuit 16, the discharge time ($T_{1b}$) from the start of the discharge until the output from the A/D converter 11 drops to the reference supply value ($E_{ref}$) is computed based on the count number at the counter 15. As noted before, the discharge time ($T_{1b}$) reflects the output from the biosensor 2 in the charge time ($T_{1a}$). Therefore, based on the discharge time ($T_{1b}$), the response current can be obtained as a voltage value.

In S18, when it is determined in the control circuit 16 that the response value does not exceed the threshold ($E_{10}$) (See FIG. 5) (S18: NO), the process steps of S11 to S18 are repeated until the response value is determined to exceed the threshold ($E_{10}$) (See FIG. 5) in S18 (S18: YES).

When it is determined in the control circuit 16 that the sampling time ($T_1$) is finished before the output from the A/D converter 11 drops to the reference supply value ($E_{ref}$) of the second reference supply 13C in S16 (S16: YES) or the response value is determined to exceed the threshold ($E_{10}$) (See FIG. 5) in S18 (S18: YES), the blood is determined to be supplied to the biosensor 2 (S19), and the sample supply confirmation process is finished.

The fact that the supply of the blood to the biosensor 2 is confirmed in the control circuit 16 means that the blood has reached at least the working electrode 20A of the biosensor 2. In this case, the reagent portion 24 (See FIGS. 2-4) is dissolved to establish a liquid phase reaction system in the flow path 23. In the liquid phase reaction system, glucose is oxidized, whereas the electron mediator is reduced. By applying a DC voltage utilizing the working electrode 20A and the counter electrode 20B, the electron mediator is oxidized, and the electrons emitted are supplied to the working electrode 20A and measured as the response current.

As shown in FIG. 8, after the blood supply confirmation (S4) is completed, the response value measurement (S5) is performed. The response value measurement (S5) is performed following the process steps shown in FIG. 10. Specifically, the control circuit 16 first resets the count number at the counter 15 and causes the counter 15 to start counting clockpulse signals (S21) and determines whether or not a predetermined time period has elapsed from the start of counting, i.e., whether or not the settling time ($T_{2c}$) (see FIG. 7B) is finished (S22). The determination is made in the control circuit 16 based on whether or not the count number at the counter 15 has reached the count number corresponding to the settling time ($T_{2c}$).

Figure 10:
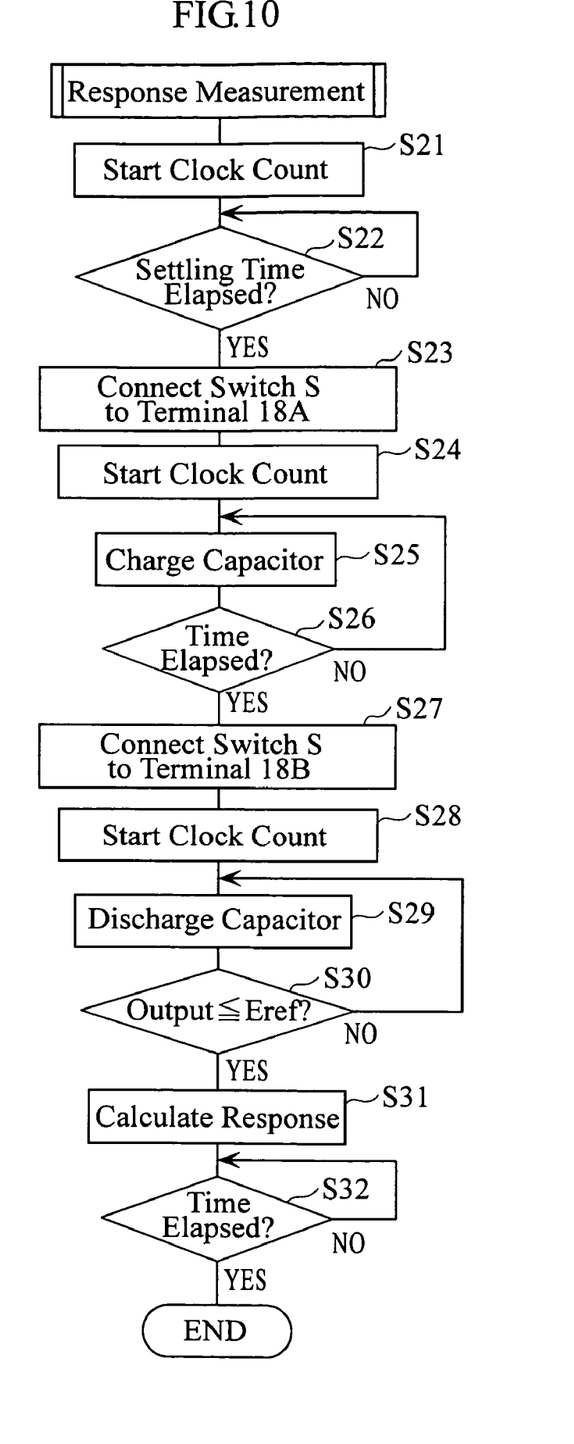
FIG. 10 is a flowchart showing the process of response value measurement in the analytical apparatus.

Subsequently, the control circuit 16 connects the switch S to the terminal 18A (S23). Then, the control circuit resets the count number at the counter 15 and causes the counter 15 to start counting the clockpulse signals (S24). By connecting the switch S to the terminal 18A, the biosensor 2 is connected to the A/D converter 11, and electric charge is stored in the capacitor 11A of the A/D converter 11 due to the current generated at the biosensor 2 (S25).

In the control circuit 16, a determination is made as to whether or not a predetermined time period has elapsed from the start of charge of the capacitor 11A, i.e., the charge time ($T_{2a}$) (See FIG. 7B) is finished (S26). The determination is made by checking whether or not the count number of the clockpulse signals at the counter 15 has reached the count number corresponding to the charge time ($T_{2a}$). The check is repetitively performed until it is determined in the control circuit 16 that the predetermined time period has elapsed, i.e., the charge time ($T_{2a}$) is finished (S26: YES) (S25, S26).

When it is determined in the control circuit 16 that the charge time ($T_{2a}$) is finished (S26: YES), the control circuit 16 connects the switch S to the terminal 18B (S27). Then, after resetting the count number at the counter 15, the control circuit causes the counter 15 to start counting the clockpulse signals (S28). Thus, the non-inverting input 11Ba of the A/D converter 11 is grounded, and the electric charge is discharged from the capacitor 11A (S29).

The control circuit 16 determines whether or not the output from the A/D converter 11 is not greater than the reference supply value ($E_{ref}$) of the second reference supply 13C (S30) Similarly to the blood supply confirmation process (S4), the determination is made by checking, in the control circuit 16, whether the output from the comparator 13 is "1" or "0".

When it is determined that the output from the A/D converter 11 is not no greater than the reference supply value ($E_{ref}$) of the second reference supply 13C (S30: NO), the control circuit 16 continues the discharge from the capacitor 11A (S29). The control circuit 16 controls the switch S and so on to repeat the discharge in S29 and the determination in S30 until it is determined in S30 that the output from the A/D converter 11 is not greater than the reference supply value ($E_{ref}$) of the second reference supply 13C (S30: YES).

When it is determined in S30 that the output from the A/D converter 11 is not greater than the reference supply value ($E_{ref}$) of the second reference supply 13C in S30 (S30: YES), the response value, i.e., the output from the biosensor 2 in the charge time ($T_{2a}$) is computed (S31). Specifically, the discharge time ($T_{2b}$) from the start of the discharge till when the output from the A/D converter 11 drops to the reference supply value ($E_{ref}$) of the second reference supply 13C is computed. Based on the discharge time ($T_{2b}$), the response value is computed as a voltage value.

Subsequently, a determination is made as to whether or not a predetermined time period ($=T_2-(T_{2c}+T_{2a})$) (See FIG. 7B) has elapsed from the start of the discharge of the capacitor 11A, i.e., the sampling time ($T_2$) is finished (S32). The determination is made by checking, in the control circuit 16, whether or not the count number of the clockpulse signals at the counter 15 has reached the count number corresponding to the predetermined time period ($=T_2-(T_{2c}+T_{2a})$). When it is determined in S32 that the sampling time ($T_2$) is finished (S32: YES), the response value measurement is completed.

As shown in FIG. 8, after the response value measurement (S5) is completed, a determination is made as to whether or not a predetermined time period T (See FIG. 5) has elapsed from when the supply of the blood is confirmed in the control circuit 16 (S6). That is, a determination is made as to whether or not the previous response value measurement (S5) corresponds to the sampling to be utilized for computing the blood glucose level. When it is determined in the control circuit 16 that the predetermined time period T has not elapsed (S6: NO), the response value measurement (S5) is repetitively performed until it is determined that the predetermined time period T has elapsed (S6: YES).

When it is determined in the control circuit 16 that the predetermined time period T has elapsed (S6: YES), the response value obtained in the most recent measurement is employed as the response value for the computation (S7), and the blood glucose level is computed based on that response value. As noted before, the computation of the blood glucose level is performed by applying the response value to a calibration curve.

As noted above, to accurately grasp the response current using the A/D converter 11 (double integration circuit) shown in FIG. 1, the input to the inverting input 11Ba and the input to the non-inverting input 11Bb need be accurately compared with each other in the operational amplifier 11B, and the discharge time ($T_{1b}$), ($T_{2b}$) (See FIGS. 7A and 7B) need be measured accurately. For this purpose, it is preferable to set the charge time ($T_{1a}$), ($T_{2a}$) of the capacitor 11A relatively long. When the charge time ($T_{1a}$), ($T_{2a}$) is short, the measurement accuracy of the response current deteriorates. On the other hand, when the charge time ($T_{1a}$), ($T_{2a}$) is long, the discharge time ($T_{1b}$), ($T_{2b}$) becomes long correspondingly. Further, to cause the output from the A/D converter 11 to come close to the reference supply value ($E_{ref}$) of the second reference supply 13C, the settling time ($T_{2c}$) needs to be set long, and the sampling time ($T_1$), ($T_2$) as well needs to be set long.

Figure 7B:
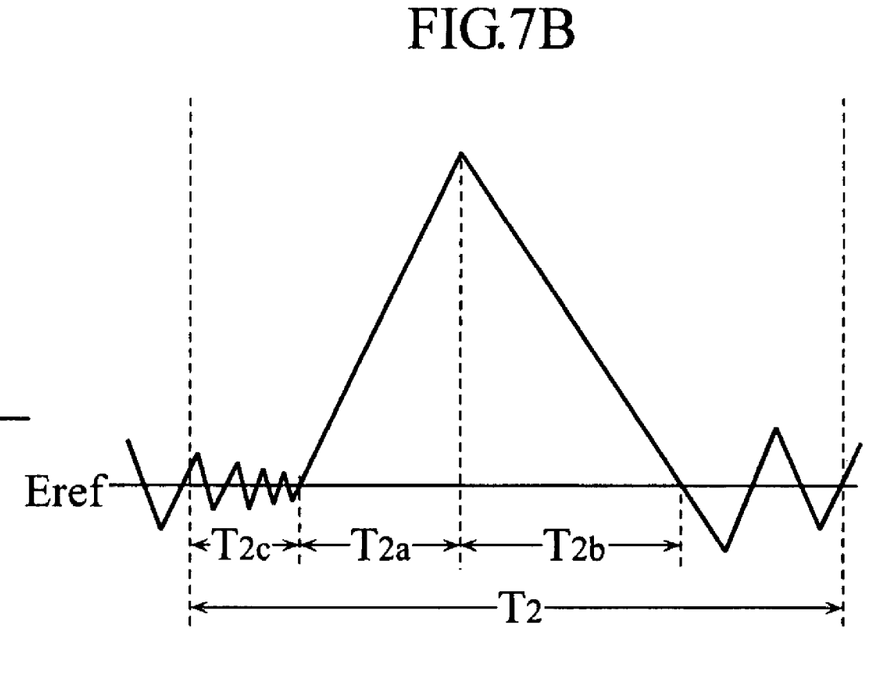
FIG. 7B shows the output waveform of one cycle after the confirmation of the blood supply.

However, as will be understood from FIGS. 7A and 7B, the control circuit 16 (See FIG. 1) of the analytical apparatus 1 performs control so that the sampling time ($T_1$) and the charge time ($T_{1a}$) of the capacitor 11A in grasping the response current to confirm the blood supply to the biosensor 2 becomes relatively short. On the other hand, in grasping the response current to compute the blood glucose level, the control circuit 16 (See FIG. 1) performs control so that the sampling time ($T_2$) and the charge time ($T_{2a}$) of the capacitor 11A become relatively long.

Therefore, in the analytical apparatus 1, the difference between the time when the supply of blood to the biosensor 2 is detected and the time when the blood is actually supplied to the biosensor 2 is small. Further, the response value for computing the blood glucose level can be grasped accurately. As a result, variations of the period from when the blood is supplied until the sampling of the response current for the computation can be suppressed, and the blood glucose level can be measured accurately.

In this embodiment, the response value measurement is performed a plurality of times in the period from when the sample supply is confirmed until when the response value for computing the blood glucose level is sampled. The response value for computing the blood glucose level is sampled after a predetermined time period has elapsed from the confirmation of the blood supply. In the present invention, however, it is only necessary to conduct the response current measurement at least once when the predetermined time period has elapsed. The response value may be measured a plurality of times before the predetermined time period elapses, and the blood glucose level may be computed based on the integration of the plurality of response values.

The present invention is also applicable to an analytical apparatus for performing the analysis of a component other than glucose (e.g., cholesterol or lactic acid) which is contained in blood or to the analysis of a sample other than blood (such as urine or saliva).

The invention claimed is:

1. A sample analysis method comprising: a first step of confirming that a sample is supplied to an analytical tool based on output from the analytical tool; a second step of grasping a level of the output from the analytical tool in a predetermined time period after the supply of the sample to the analytical tool is confirmed, the grasping being performed at least once including at a time point when the predetermined time period has elapsed; and a third step of performing computation necessary for the analysis of the sample;

wherein the grasping of the output from the analytical tool in the first step and the second step is performed based on output from a double integration circuit which is obtained by inputting the output from the analytical tool into the double integration circuit;

wherein the first step comprises grasping a level of the output from the double integration circuit repetitively at a first sampling time interval defined by a time period from start of the inputting into the double integration circuit until completion of the outputting from the double integration circuit; and wherein, the second step comprises grasping a level of the output from the double integration circuit at a second sampling time interval defined by a time period from start of the inputting into the double integration circuit until completion of the outputting from the double integration circuit, the second sampling time interval being set longer than the first sampling time interval.

2. The sample analysis method according to claim 1, wherein the second step comprises performing the inputting of the output from the analytical tool into the double integration circuit and the outputting from the double integration circuit repetitively at the second time interval, and grasping the output from the analytical tool at a time point when the predetermined time period has elapsed.

3. The sample analysis method according to claim 1, wherein the first sampling time interval is selected from a range of 10 to 30 msec, whereas the second sampling time interval is selected from a range of 30 to 300 msec.

4. The sample analysis method according to claim 1, wherein the double integration circuit includes a capacitor for storing the output from the analytical tool as an electric charge and then discharging the stored electric charge and is capable of grasping the output from the analytical tool based on a discharge time of the capacitor; and wherein a charge time of the capacitor in the first sampling time interval in the first step is shorter than a charge time of the capacitor in the second sampling time interval in the second step.

5. The sample analysis method according to claim 4, wherein the charge time of the capacitor in the first sampling time interval in the first step is selected from a range of 5 to 15 msec; and wherein the charge time of the capacitor in the second sampling time interval in the second step is selected from a range of 15 to 150 msec.

6. The sample analysis method according to claim 1, wherein the analytical tool includes an electrode for outputting an amount of electron transfer between the electrode and a particular component as an electric physical quantity.

7. The sample analysis method according to claim 6, wherein the analytical tool includes a reagent portion containing at least one reagent for promoting the electron transfer between the particular component and said electrode, and an additional electrode for applying, together with said electrode, voltage to a reaction system of the sample and said at least one reagent; and wherein the electric physical quantity is outputted from the analytical tool as a current value by applying voltage to the reaction system using said electrode and the additional electrode.

8. The sample analysis method according to claim 1, wherein the analytical tool is designed to use blood as the sample.

9. A sample analysis apparatus to be used with an analytical tool mounted thereto for analyzing a sample supplied to the analytical tool based on output from the analytical tool, the apparatus comprising: a double integration circuit into which the output from the analytical tool is inputted and which outputs a physical quantity related to the input; and a controller for controlling timing at which the output from the analytical tool is inputted into the double integration circuit and timing at which the physical quantity is outputted from the double integration circuit;

wherein the controller performs control so that a time interval from start of the inputting into the double integration circuit until start of the outputting from the double integration circuit becomes longer after the supply of the sample to the analytical tool is confirmed than before the supply of the sample to the analytical tool is confirmed.

10. The sample analysis apparatus according to claim 9, wherein the double integration circuit includes a capacitor for storing the output from the analytical tool as an electric charge and then discharging the stored electric charge and is capable of grasping the output from the analytical tool based on a discharge time of the capacitor; and wherein the controller performs control so that the charge time of the capacitor becomes longer after the supply of the sample to the analytical tool is confirmed than before the supply of the sample to the analytical tool is confirmed.

11. The sample analysis apparatus according to claim 10, wherein, when the analytical tool includes an electrode for outputting an electric physical quantity, the apparatus further comprises a switch for selecting a state in which the double integration circuit is directly or indirectly connected to ground or a state in which the double integration circuit is connected to the electrode; and wherein the controller controls the switch to control the timing at which the output from the analytical tool is inputted into the double integration circuit and the timing at which the physical quantity is outputted from the double integration circuit.

* * * * *